United States Patent [19]

Reinehr et al.

[11] Patent Number: 6,080,208
[45] Date of Patent: Jun. 27, 2000

[54] STILBENE COMPOUNDS AND THEIR USE

[75] Inventors: Dieter Reinehr, Kandern, Germany; Georges Metzger, Moernach, France; Hanspeter Sauter, Schopfheim, Germany

[73] Assignee: Ciba Specialty Chemicals Corporation, Tarrytown, N.Y.

[21] Appl. No.: 09/218,246

[22] Filed: Dec. 22, 1998

Related U.S. Application Data

[62] Division of application No. 08/862,036, May 22, 1997, Pat. No. 5,892,031.

[30] Foreign Application Priority Data

May 23, 1996 [GB] United Kingdom .................. 9610832

[51] Int. Cl.$^7$ .......................... C07D 251/00; D06P 5/02; C11D 3/28
[52] U.S. Cl. .................... 8/115.7; 8/119; 8/442; 510/302; 510/307; 510/309; 510/324; 510/346; 510/377; 510/394; 252/301.21; 252/301.23; 544/193.2; 544/113; 544/83
[58] Field of Search ...................... 8/115.7, 119, 115.54, 8/442; 510/302, 307, 309, 324, 346, 377, 394; 252/301.21, 301.23; 544/193.2, 113, 83

[56] References Cited

U.S. PATENT DOCUMENTS

| 2,612,501 | 9/1952 | Wilson .................................. 260/247.1 |
| 5,518,657 | 5/1996 | Fringeli et al. ..................... 252/301.23 |
| 5,744,599 | 4/1998 | Reinehr et al. ....................... 544/193.1 |
| 5,939,379 | 8/1999 | Eckhardt et al. ........................ 510/516 |

FOREIGN PATENT DOCUMENTS

| 0509787 | 10/1992 | European Pat. Off. . |
| 0542677 | 5/1993 | European Pat. Off. . |
| 0693483 | 1/1996 | European Pat. Off. . |
| 0704444 | 4/1996 | European Pat. Off. . |
| 0728749 | 8/1996 | European Pat. Off. . |
| 943639 | 12/1963 | United Kingdom . |
| 997044 | 6/1965 | United Kingdom . |
| 1093507 | 12/1967 | United Kingdom . |
| 1173806 | 12/1969 | United Kingdom . |
| 1174631 | 12/1969 | United Kingdom . |
| 1317465 | 5/1973 | United Kingdom . |
| 1337583 | 11/1973 | United Kingdom . |
| 2158454 | 11/1985 | United Kingdom . |
| 2298422 | 9/1996 | United Kingdom . |
| 9404515 | 3/1994 | WIPO . |

OTHER PUBLICATIONS

Chem. Abstr. 116:151801 JP 03279369 A2 Dec. 10, 1991.
Chem. Abstr. 77:12261 Fluorescent Whiteners for Photographic Paper I. V. Aleksandrov et al. Russian Journal 17(2) 1972 No Month Given.

*Primary Examiner*—Yogendra Gupta
*Assistant Examiner*—Brian P. Mruk
*Attorney, Agent, or Firm*—Kevin T. Mansfield

[57] ABSTRACT

The present invention provides new stilbene compounds which are useful as fluorescent whitening agents (FWAs), imparting high whiteness levels to textile fibre material treated with them, and which also impart a high sun protection factor (SPF) to textile fibre material treated with them. The present invention also concerns a method of imparting a high whiteness level and a high sun protection factor to textile fibre material, especially cotton, polyamide and wool, comprising treating the textile material with the new compounds.

28 Claims, No Drawings

STILBENE COMPOUNDS AND THEIR USE

This application is a divisional of prior application Ser. No. 08/862,036, filed May 22, 1997, now U.S. Pat. No. 5,892,031.

The present invention relates to new stilbene compounds which are useful as fluorescent whitening agents (FWAs), imparting high whiteness levels to textile fibre material treated with them, and which also impart a high sun protection factor (SPF) to textile fibre material treated with them. The present invention also concerns a method of imparting a high whiteness level and a high sun protection factor to textile fibre material, especially cotton, polyamide and wool, comprising treating the textile material with the new compounds.

It is known that light radiation of wavelengths 280–400 nm permits tanning of the epidermis. It is also known that rays of wavelengths 280–320 nm (termed UV-B radiation), cause erythemas and skin burning which can inhibit skin tanning.

Radiation of wavelengths 320–400 nm (termed UV-A radiation) is known to induce skin tanning but can also cause skin damage, especially to sensitive skin which is exposed to sunlight for long periods. Examples of such damage include loss of skin elasticity and the appearance of wrinkles, promotion of the onset of erythemal reaction and the inducement of phototoxic or photoallergic reactions.

Any effective protection of the skin from the damaging effects of undue exposure to sunlight clearly needs to include means for absorbing both UV-A and UV-B components of sunlight before they reach the skin surface.

Traditionally, protection of exposed human skin against potential damage by the UV components in sunlight has been effected by directly applying to the skin a preparation containing a UV absorber. In areas of the world, e.g. Australia and America, which enjoy especially sunny climates, there has been a great increase in the awareness of the potential hazards of undue exposure to sunlight, compounded by fears of the consequences of alleged damage to the ozone layer. Some of the more distressing embodiments of skin damage caused by excessive, unprotected exposure to sunlight are development of melanomas or carcinomas on the skin.

One aspect of the desire to increase the level of skin protection against sun light has been the consideration of additional measures, over and above the direct protection of the skin. For example, consideration has been given to the provision of protection to skin covered by clothing and thus not directly exposed to sunlight.

Most natural and synthetic textile materials are at least partially permeable to UV components of sunlight. Accordingly, the mere wearing of clothing does not necessarily provide skin beneath the clothing with adequate protection against damage by UV radiation. Although clothing containing a deeply coloured dye and/or having a tight weave texture may provide a reasonable level of protection to skin beneath it, such clothing is not practical in hot sunny climates, from the standpoint of the personal comfort of the wearer.

There is a need, therefore, to provide protection against UV radiation for skin which lies underneath clothing, including lightweight summer clothing, which is undyed or dyed only in pale shades. Depending on the nature of the dyestuff, even skin beneath clothing dyed in some dark shades may also require protection from UV radiation.

Such lightweight summer clothing normally has a density of less than 200 g/m$^2$ and has a sun protection factor rating between 1.5 and 20, depending on the type of fibre from which the clothing is manufactured.

The SPF rating of a sun protectant (sun cream or clothing) may be defined as the multiple of the time taken for the average person wearing the sun protectant to suffer sun burning under average exposure to sun. For example, if an average person would normally suffer sun burn after 30 minutes under standard exposure conditions, a sun protectant having an SPF rating of 5 would extend the period of protection from 30 minutes to 2 hours and 30 minutes. For people living in especially sunny climates, where mean sun burn times are minimal, e.g. only 15 minutes for an average fair-skinned person at the hottest time of the day, SPF ratings of at least 20 are desired for lightweight clothing.

It is already known, e.g. from WO94/4515, that the application of specified types of UVA to a light-weight textile materials in general can effect an increase in the SPF value of the textile so treated. The increase in SPF value achieved thereby, however, is relatively modest.

The use of FWAs in order to effect an increase in the SPF value of textiles has also been proposed. Most FWAs, however, are only effective in absorbing radiation in the UV-A range.

Certain new stilbene compounds have now been found which can be readily produced and which, unexpectedly, absorb radiation in both the UV-A and UV-B ranges, and impart greatly increased SPF ratings to textile fibre materials treated with the new compounds.

Accordingly, the present invention provides, as a first aspect, a compound having the formula:

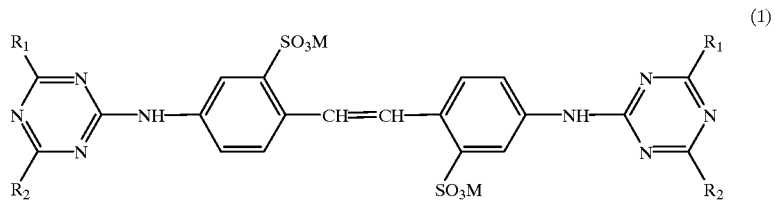

(1)

in which M is hydrogen, an alkali metal atom, ammonium or a cation formed from an amine;

$R_1$ is a group having the formulae:

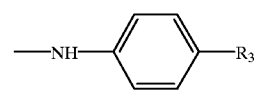

in which $R_3$ is $NR_4R_5$ in which $R_4$ and $R_5$, independently, are hydrogen, $C_1$–$C_{20}$alkyl, $C_2$–$C_{20}$alkyl which is interrupted by from 1 to 6 oxygen atoms, hetero-substituted $C_1$–$C_{20}$alkyl, $C_6$–$C_{10}$aryl or $C_7$–$C_{13}$aralkyl; or NH—CO—$R_6$ in which $R_6$ is $C_1$–$C_{20}$alkyl, $C_2$–$C_{20}$alkyl which is interrupted by from 1 to 6 oxygen atoms, hetero-substituted $C_1$–$C_{20}$alkyl, $C_5$–$C_{12}$cycloalkyl, $C_6$–$C_{10}$aryl or $C_7$–$C_{13}$aralkyl;
or the formula:

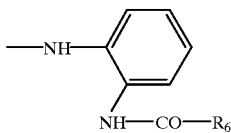

in which $R_6$ has its previous significance; and
$R_2$ is $NH_2$, $N(CH_2CH_2OH)_2$, $N[CH_2CH(OH)CH_3]_2$, NH—$C_1$–$C_{20}$alkyl, NH—$C_6$–$C_{10}$aryl,

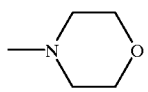

O—$C_1$–$C_{20}$alkyl or O—$C_6$–$C_{10}$aryl; provided that the compound of formula (1) in which $R_1$ is

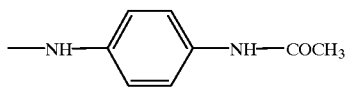

and $R_2$ is

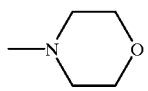

is excluded.
The compound of formula (1) in which $R_1$ is

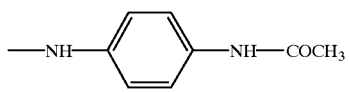

and $R_2$ is

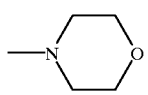

is described in U.S. Pat. No. 2612501 together with its use as a fluorescent whitening agent for textiles.

$C_1$–$C_{20}$alkyl groups $R_4$, $R_5$ and $R_6$ may be branched or unbranched such as methyl, ethyl, n-propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, n-nonyl, n-decyl, n-undecyl, 1-methylundecyl, n-dodecyl, 1,1,3,3,5,5-hexamethylhexyl, n-tridecyl, n-tetradecyl, n-pentadecyl, n-hexadecyl, n-heptadecyl, n-octadecyl and n-eicosyl, preferably methyl or ethyl.

O—$C_1$–$C_{20}$alkyl groups $R_2$ may be branched or unbranched such as methoxy, ethoxy, n-propoxy, isopropoxy, n-butoxy, sec-butoxy, isobutoxy, t-butoxy, 2-ethylbutoxy, n-pentoxy, isopentoxy, 1-methylpentoxy, 1,3-dimethylbutoxy, n-hexoxy, 1-methylhexoxy, n-heptoxy, isoheptoxy, 1,1,3,3-tetramethylbutoxy, 1-methylheptoxy, 3-methylheptoxy, n-octoxy, 2-ethylhexoxy, 1,1,3-trimethylhexoxy, 1,1,3,3-tetramethylpentoxy, n-nonoxy, n-decoxy, n-undecoxy, 1-methylundecoxy, n-dodecoxy, 1,1,3,3,5,5-hexamethylhexoxy, n-tridecoxy, n-tetradecoxy, n-pentadecoxy, n-hexadecoxy, n-heptadecoxy, n-octadecoxy and n-eicosoxy, preferably methoxy, ethoxy or propoxy groups, especially methoxy groups.

When $R_4$, $R_5$ and $R_6$ are $C_2$–$C_{20}$alkyl which is interrupted by from 1 to 6 oxygen atoms, these groups may be branched or unbranched such as 3-oxabutyl, 3-oxapentyl, 3-oxahexyl, 3-oxaoctyl, 3-oxadecyl, 3-oxadodecyl, 3-oxatetradecyl, 3-oxahexadecyl, 3-oxaoctadecyl, 3,6-dioxaheptyl, 3,6-dioxaoctyl, 3,6-dioxadecyl, 3,6-dioxadodecyl, 3,6-dioxatetradecyl, 3,6-dioxaheptadecyl, 3,6,9-trioxadecyl, 3,6,9-trioxaundecyl, 3,6,9-trioxadodecyl, 3,6,9-trioxatetradecyl, 3,6,9-trioxahexadecyl or 3,6,9-trioxadecaheptyl.

When $R_4$, $R_5$ and $R_6$ are $C_1$–$C_{20}$alkyl which is substituted by a heterocyclic residue, they may be any of the $C_1$–$C_{20}$alkyl groups listed above in relation to $C_1$–$C_{20}$alkyl groups $R_4$, $R_5$ and $R_6$, preferably methyl, ethyl or propyl groups, especially a methyl group, substituted by a morpholinyl, piperidyl, 2,2,6,6-tetramethylpiperidyl, piperazinyl or N-methylpiperazinyl residue.

$C_5$–$C_{12}$cycloalkyl groups $R_6$ are preferably, cyclopentyl, cyclohexyl, cyclooctyl, cyclodecyl or cyclododecyl groups, especially a cyclohexyl group.

When $R_4$, $R_5$ and $R_6$ are $C_6$–$C_{10}$aryl, they are a naphthyl or, preferably, a phenyl group.

$C_7$–$C_{20}$aralkyl groups $R_4$, $R_5$ and $R_6$ may be naphthylalkyl groups but are preferably phenylalkyl groups. Examples of $C_7$–$C_{20}$ phenylalkyl groups $R_4$, $R_5$ and $R_6$ include benzyl, α-methylbenzyl, α,α-dimethylbenzyl, phenylethyl, phenylpropyl, phenyl-butyl, phenylpentyl, phenylhexyl, phenylheptyl, phenyloctyl, phenynonyl, phenyidecyl, phenyldodecyl and phenyltetradecyl.

$C_6$–$C_{10}$aryl groups $R_4$, $R_5$ and $R_6$, O—$C_6$–$C_{10}$aryl groups $R_2$, NH—$C_6$–$C_{10}$aryl groups $R_2$ and $C_7$–$C_{20}$aralkyl groups $R_4$, $R_5$ and $R_6$ may be unsubstituted or may be substituted by one of more substituents. Examples of such substituent groups include hydroxyl, —$NH_2$, —$NHR_1$, —$NR_1R_2$ (in which $R_1$ and $R_2$ have their previous significance), halogen, $C_1$–$C_{20}$alkyl, $C_1$–$C_{20}$alkoxy, $C_2$–$C_{20}$alkenyl, $C_3$–$C_{20}$alkynyl, $C_6$–$C_{12}$aryl, sulfonyl, carboxyl, (meth)acryloxy or (meth)acrylamino.

In each of the compounds of formula (1) it is preferred that they are used in neutral form, i.e. that M is other than hydrogen, preferably a cation formed from an alkali metal, in particular sodium, or from an amine.

In the compounds of formula (1), preferably $R_1$ is a group of formula:

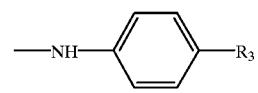

in which $R_3$ has its previous significance and is preferably NH—CO—$R_6$ in which $R_6$ has its previous significance and is preferably $C_1$–$C_4$alkyl, especially methyl; and preferably $R_2$ is $NH_2$ or

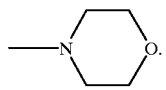

The compounds of formula (1) may be produced by reacting, under known reaction conditions, cyanuric chloride, successively, in any desired sequence, with each of an aminostilbene-sulfonic acid, an amino compound capable of introducing a group $R_1$ and a compound capable of introducing a group $R_2$, in which $R_1$ and $R_2$ each have their previous significance.

The starting materials are known compounds which are readily available.

The present invention also provides, as a second aspect, a method for the fluorescent whitening and for the improvement of the SPF of a textile fibre material, comprising treating the textile fibre material with 0.05 to 3.0% by weight, based on the weight of the textile fibre material, of one or more compounds having the formula:

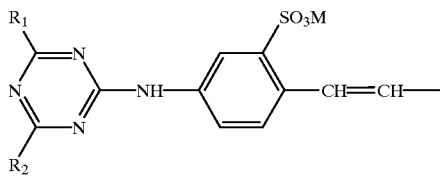

(1A)

in which M is hydrogen, an alkali metal atom, ammonium or a cation formed from an amine;

$R_1$ is a group having the formula:

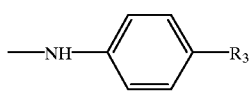

in which $R_3$ is $NR_4R_5$ in which $R_4$ and $R_5$, independently, are hydrogen, $C_1-C_{20}$alkyl, $C_2-C_{20}$alkyl which is interrupted by from 1 to 6 oxygen atoms, hetero-substituted $C_1-C_{20}$alkyl, $C_6-C_{10}$aryl or $C_7-C_{13}$aralkyl; or NH—CO—$R_6$ in which $R_6$ is $C_1-C_{20}$alkyl, $C_2-C_{20}$alkyl which is interrupted by from 1 to 6 oxygen atoms, hetero-substituted $C_1-C_{20}$alkyl, $C_5-C_{12}$cycloalkyl, $C_6-C_{10}$aryl or $C_7-C_{13}$aralkyl;
or the formula:

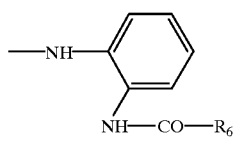

in which $R_6$ has its previous significance; and
$R_2$ is $NH_2$, $N(CH_2CH_2OH)_2$, $N[CH_2CH(OH)CH_3]_2$, NH—$C_1-C_{20}$alkyl, NH—$C_6-C_{10}$aryl,

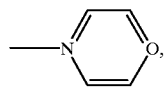

O—$C_1-C_{20}$alkyl or O—$C_6-C_{10}$aryl.

The textile fibres treated according to the method of the present invention may be natural or synthetic fibres or mixtures thereof. Examples of natural fibres include vegetable fibres such as cotton, viscose, flax, rayon or linen, preferably cotton and animal fibres such as wool, mohair, cashmere, angora and silk, preferably wool. Synthetic fibres include polyester, polyamide and polyacrylonitrile fibres. Preferred textile fibres are cotton, polyamide and wool fibres.

Preferably, textile fibres treated according to the method of the present invention have a density of less than 200 g/m² and have not been previously dyed in deep shades.

Some of the compounds of formula (1A) used in the method of the present invention may be only sparingly soluble in water and may need to be applied in dispersed form. For this purpose, they may be milled with an appropriate dispersant, conveniently using quartz balls and an impeller, down to a particle size of 1–2 microns.

As dispersing agents for such sparingly-soluble compounds of formula (1A) there may be mentioned:

acid esters or their salts of alkylene oxide adducts, e.g., acid esters or their salts of a polyadduct of 4 to 40 moles of ethylene oxide with 1 mole of a phenol, or phosphoric acid esters of the adduct of 6 to 30 moles of ethylene oxide with 1 mole of 4-nonylphenol, 1 mole of dinonylphenol or, especially, with 1 mole of compounds which have been produced by the addition of 1 to 3 moles of styrenes on to 1 mole of phenol;

polystyrene sulphonates;

fatty acid taurides;

alkylated diphenyloxide-mono- or -di-sulphonates;

sulphonates of polycarboxylic acid esters;

addition products of 1 to 60, preferably 2 to 30 moles of ethylene oxide and/or propylene oxide on to fatty amines, fatty amides, fatty acids or fatty alcohols, each having 8 to 22 carbon atoms, or on to tri- to hexavalent $C_3-C_6$alkanols, the addition products having been converted into an acid ester with an organic dicarboxylic acid or with an inorganic polybasic acid;

lignin sulphonates; and, in particular formaldehyde condensation products, e.g., condensation products of lignin sulphonates and/or phenol and formaldehyde; condensation products of formaldehyde with aromatic sulphonic acids, e.g., condensation products of ditolylethersulphonates and formaldehyde; condensation products of naphthalenesulphonic acid and/or naphthol- or naphthylaminesulphonic acids and formaldehyde; condensation products of phenolsulphonic acids and/or sulphonated dihydroxydiphenylsulphone and phenols or cresols with formaldehyde and/or urea; or condensation products of diphenyloxide-disulphonic acid derivatives with formaldehyde.

Depending on the type of compound of formula (1A) used, it may be beneficial to carry out the treatment in a neutral, alkaline or acidic bath. The method is usually conducted in the temperature range of from 20 to 140° C., for example at or near to the boiling point of the aqueous bath, e.g. at about 90° C.

Solutions of the compound of formula (1A), or its emulsions in organic solvents may also be used in the method of the present invention. For example, the so-called solvent dyeing (pad thermofix application) or exhaust dyeing methods in dyeing machines may be used.

If the method of the present invention is combined with a textile treatment or finishing method, such combined treatment may be advantageously carried out using appropriate stable preparations which contain the compound of formula (1A) in a concentration such that the desired SPF improvement is achieved.

In certain cases, the compound of formula (1A) is made fully effective by an after-treatment. This may comprise a chemical treatment such as treatment with an acid, a thermal treatment or a combined thermal/chemical treatment.

It is often advantageous to use the compound of formula (1A) in admixture with an assistant or extender such as anhydrous sodium sulfate, sodium sulfate decahydrate, sodium chloride, sodium carbonate, an alkali metal phosphate such as sodium or potassium orthophosphate, sodium or potassium pyrophosphate or sodium or potassium tripolyphosphate, or an alkali metal silicate such as sodium silicate.

In addition to the compounds of formula (1A), a minor proportion of one or more adjuvants may also be employed in the method of the present invention. Examples of adjuvants include emulsifiers, perfumes, colouring dyes, opacifiers, further fluorescent whitening agents, bactericides, nonionic surfactants, fabric care ingredients, especially fabric softeners, stain release or stain repellant ingredients or water-proofing agents, anti-gelling agents such as nitrites or nitrates of alkali metals, especially sodium nitrate, and corrosion inhibitors such as sodium silicate.

The amount of each of these optional adjuvants should not exceed 1%, and preferably ranges from 0.01 to 1% by weight on the treated fibre.

The method of the present invention, in addition to providing fluorescent whitening of a textile article treated according to the present invention and sunscreen protection to the skin covered by a textile article so treated, may also increases the useful life of a textile article so treated. In particular, the tear resistance and/or lightfastness of the treated textile fibre material may be improved.

The present invention also provides a textile fabric produced from a fibre treated according to the method of the present invention as well as an article of clothing produced from the said fabric.

Such textile fabrics and articles of clothing produced from the said fabrics typically have an SPF rating of 20 and above whereas untreated cotton, for example, generally has an SPF rating of from 2 to 4.

The treatment method according to the present invention may also be conducted by washing the textile fibre material with a detergent containing at least one compound of formula (1A), thereby imparting an excellent fluorescent whiteness level and an outstanding sun protection factor to the fibre material so washed.

The detergent treatment according to the present invention is preferably effected by washing the textile fibre material at least once with the detergent composition at a temperature ranging from 10 to 100° C., especially from 15 to 60° C.

The detergent composition used preferably comprises:
i) 5–90%, preferably 5–70% of an anionic surfactant and/or a nonionic surfactant;
ii) 5–70%, preferably 5–40% of a builder;
iii) 0–30%, preferably 1–12% of a peroxide;
iv) 0–10%, preferably 1–6% of a peroxide activator and/or 0–1%, preferably 0.1–3% of a bleaching catalyst;
v) 0.005–2%, preferably 0.01–1% of at least one compound of formula (1A); and
vi) 0.005–10%, preferably 0.1–5% of of one or more auxiliaries, each by weight, based on the total weight of the detergent.

The said detergent compositions are also new and, as such form a further aspect of the present invention.

The detergent may be formulated as a solid, as an aqueous liquid comprising 5–50, preferably 10–35% water or as a non-aqueous liquid detergent, containing not more than 5, preferably 0–1 wt. % of water, and based on a suspension of a builder in a non-ionic surfactant, as described, e.g., in GB-A-2158454.

The anionic surfactant component may be, e.g., a sulphate, sulphonate or carboxylate surfactant, or a mixture of these.

Preferred sulphates are alkyl sulphates having 12–22 carbon atoms in the alkyl radical, optionally in combination with alkyl ethoxy sulphates having 10–20 carbon atoms in the alkyl radical.

Preferred sulphonates include alkyl benzene sulphonates having 9–15 carbon atoms in the alkyl radical.

In each case, the cation is preferably an alkali metal, especially sodium.

Preferred carboxylates are alkali metal sarcosinates of formula R—CO(R$^1$)CH$_2$COOM$^1$ in which R is alkyl or alkenyl having 9–17 carbon atoms in the alkyl or alkenyl radical, R$^1$ is C$_1$–C$_4$ alkyl and M$^1$ is alkali metal.

The nonionic surfactant component may be, e.g., a condensate of ethylene oxide with a C$_9$–C$_{15}$ primary alcohol having 3–8 moles of ethylene oxide per mole.

The builder component may be an alkali metal phosphate, especially a tripolyphosphate; a carbonate or bicarbonate, especially the sodium salts thereof; a silicate or disilicate; an aluminosilicate; a polycarboxylate; a polycarboxylic acid; an organic phosphonate; or an aminoalkylene poly (alkylene phosphonate); or a mixture of these.

Preferred silicates are crystalline layered sodium silicates of the formula NaHSi$_m$O$_{2m+1}$·pH$_2$O or Na$_2$Si$_m$O$_{2m+1}$·pH$_2$O in which m is a number from 1.9 to 4 and p is 0 to 20.

Preferred aluminosilicates are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid.

Preferred organic phosphonates or aminoalkylene poly (alkylene phosphonates) are alkali metal ethane 1-hydroxy diphosphonates, nitrilo trimethylene phosphonates, ethylene diamine tetra methylene phosphonates and diethylene triamine penta methylene phosphonates.

Any peroxide component may be any organic or inorganic peroxide compound, described in the literature or available on the market, which bleaches textiles at conventional washing temperatures, e.g. temperatures in the range of from 5° C. to 90° C. In particular, the organic peroxides are, for example, monoperoxides or polyperoxides having alkyl chains of at least 3, preferably 6 to 20, carbon atoms; in particular diperoxydicarboxylates having 6 to 12° C. atoms, such as diperoxyperazelates, diperoxypersebacates, diperoxyphthalates and/or diperoxydodecanedioates, especially their corresponding free acids, are of interest. It is preferred, however, to employ very active inorganic peroxides, such as persulphate, perborate and/or percarbonate. It is, of course, also possible to employ mixtures of organic and/or inorganic peroxides. The peroxides, especially the inorganic peroxides, are preferably activated by the inclusion of an activator such as tetraacetyl ethylenediamine or nonoyloxybenzene sulfonate. Bleaching catalysts which may be added include, e.g., enzymatic peroxide precursors and/or metal complexes. Preferred metal complexes are manganese or iron complexes such as manganese or iron phthalocyanines or the complexes described in EP-A-0509787.

The detergents used will usually contain one or more auxiliaries such as soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; enzymes, such as amylases and proteases; photobleaching agents; pigments; and/or shading agents. These constituents should, of course, be stable to any bleaching system employed.

The following Examples further illustrate the present invention. The compound of formula (101) of Example 1 has been disclosed in U.S. Pat. No. 2,612,501.

EXAMPLE 1

A solution of 17.3 g of 4,4'-diaminostilbene-2,2'-disulfonic acid (85%) in 150 mls of water and 60 g of ice is added, over 1 hour, to a solution of 12.66 g of cyanuric chloride in 80 mls of acetone and 75 g of ice. During the addition, the temperature is held at 0° C. Over a period of 10 minutes, 34.4 mls of a 1-molar soda solution are added, whereupon the pH increases from 1 to 7. The solution is treated with 10.5 g of 4-aminoacetanilide and with a further 34.4 mls of a 1-molar soda solution and heated to 50° C. using an external heating bath. After the addition of 12.6 g of morpholine, the temperature of the bath is raised to 95° C. and acetone is distilled off until the internal temperature of the reaction mixture is 90° C. After cooling the reaction mixture to 20° C., it is adjusted to pH 7.5 using 2N hydrochloric acid and treated with 3 litres of acetone. The reaction mixture is then filtered to obtain 26.4 g of a light-yellow compound of formula (101) having $\lambda_{max}$ of 283 nm and 355 nm.

Elemental analysis of the compound having the formula (101) and having the empirical formula $C_{44}H_{44}N_{14}O_{10}Na_2S_2 \cdot 8H_2O$ gives:

Req. % C, 44.66; H, 5.11; N, 16.57; S, 5.41; $H_2O$, 12.17. Found % C, 44.96; H, 5.15; N, 16.83; S, 5.03; $H_2O$, 11.81.

EXAMPLE 2

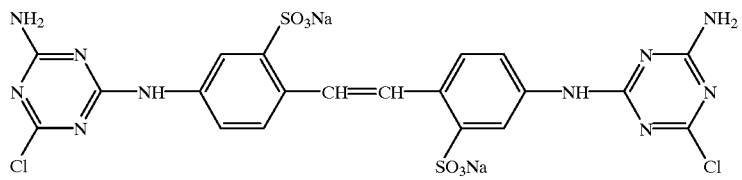

(102)

A) 12.65 g of cyanuric chloride are dissolved in 80 mls of acetone and 75 g of ice-water and then treated, dropwise, with a solution of 15 g of 4,4'-diaminostilbene-2,2'-disulfonic acid (81.6%) in 200 mls of ice-water. During the addition, the temperature is held at 0° C. After stirring the reaction mixture for 30 minutes, 10 g of a 30% ammonia solution are added and the resulting mixture is treated with 68.8 mly of a 1 molar solution of soda over 20 minutes. The reaction mixture is stirred for a further 5 hours at 50° C. After cooling to 20° C., the reaction mixture is filtered off, washed with water and dried to give 21.4 g of a light-yellow product of formula (102) having a $\lambda_{max}$ of 352 nm.

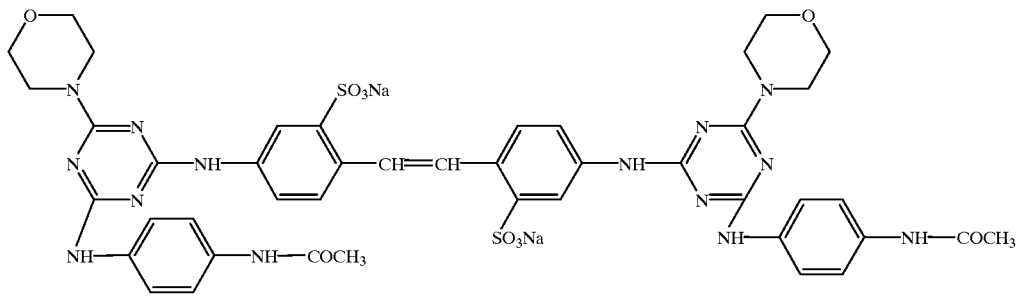

(101)

Elemental analysis of the compound having the formula (102) and having the empirical formula $C_{20}H_{14}N_{10}Cl_2S_2Na_2O_6 \cdot 10.5H_2O$ gives:

Req. % C, 27.53; H, 4.20; N, 16.05; S, 7.35; Cl, 8.13; $H_2O$, 23.06. Found % C, 27.58; H, 4.31; N, 16.53; S, 7.26; Cl, 8.31; $H_2O$, 23.06.

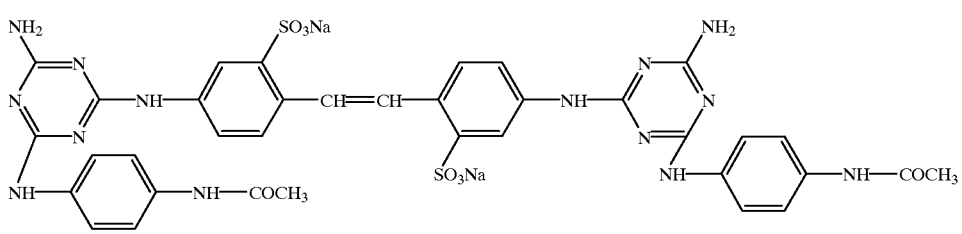

(103)

B) 10 g of the compound (102) obtained in Part A) are added, dropwise, at 100° C. over 30 minutes, to a solution of 5 g of p-aminoacetanilide in 150 mls of methylcellosolve and the reaction mixture is then heated to 130° C., whereupon the compound of formula (103) is precipitated as the free acid. The reaction is then cooled, fitered and washed with hydrochloric acid and then with water. The moist filtercake is then adjusted to pH 11 using 2N NaOH and then filtered with suction. After drying, there are obtained 9.8 g of a light-beige compound of formula (103) having a $\lambda_{max}$ of 283 nm and 352 nm.

Elemental analysis of the compound having the formula (103) and having the empirical formula $C_{36}H_{32}N_{14}S_2O_8Na_2 \cdot 7.4H_2O$ gives:

Req. % C, 41.89; H, 4.57; N, 19.00; S, 6.21; $H_2O$, 12.92. Found % C, 42.22; H, 4.48; N, 19.19; S, 6.20; $H_2O$, 12.92.

EXAMPLE 3 are suspended in 110 ml of 0.1 molar soda solution, treated with 3.3 g of a 40% solution of methylamine in water and the reaction mixture is then heated to 90° C. The compound of formula (105) is obtained according to the procedure described in Example 1 except that the final reaction step therein, namely the reaction with morpholine, is omitted. The reaction mixture is stirred at this temperature for 2 hours until the reaction is complete, as indicated by HPLC. The free acid is first precipitated in 200 ml of acetone containing 25 ml of 2N HCl. After filtration with suction and then washing with 100 ml acetone, the filter residue is suspended in methanol and converted into the di-sodium salt using 2N NaOH. After concentration by evaporation and drying in air, there remain 8.88 g (73% theory) of the compound (104).

Elemental analysis of the compound having the formula (104) and having the empirical formula $C_{38}H_{34}N_{14}O_8S_2Na_2 \cdot 9H_2O \cdot 0.4NaCl$ gives:

Req. % C, 41.00; H, 4.89; N, 17.62; S, 5.76; Na, 4.96; Cl, 1.27; $H_2O$, 14.56. Found % C, 40.82; H, 4.92; N, 17.51; S, 5.76; Na, 4.83; Cl, 1.34; $H_2O$, 14.33.

The procedure described in one or more of Examples 1 to 3 may be used to prepare the following further compounds of formula (1):

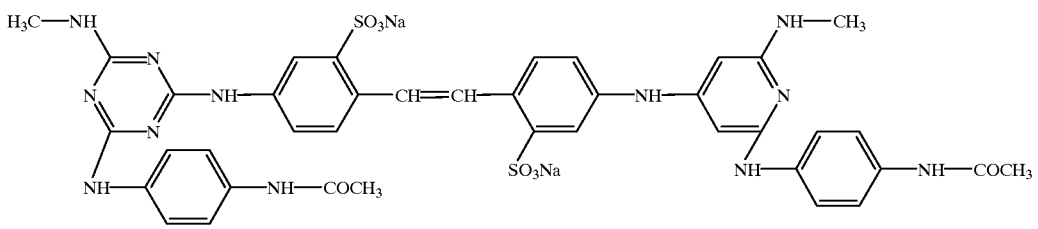

(104)

10 g of the compound having the formula:

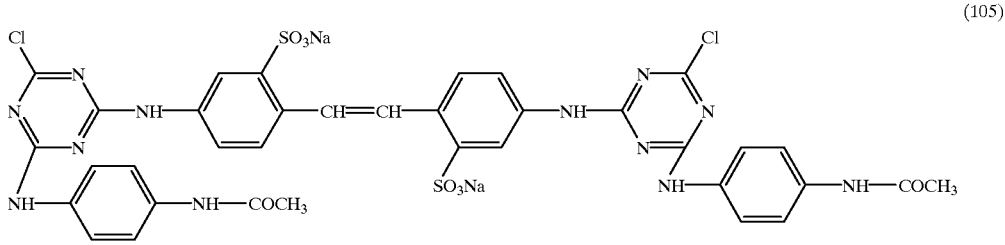

(105)

Compounds having the formula:

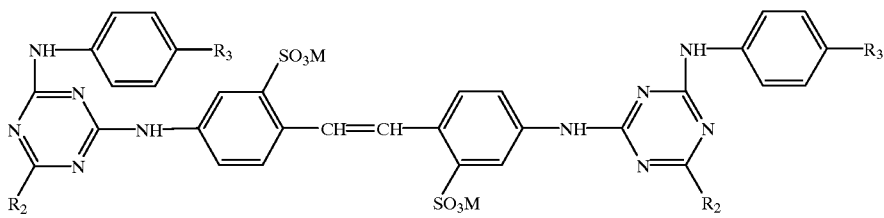

in which the substituents $R_2$, $R_3$ and M are as defined in the following Table:

| $R_2$ | $R_3$ | M |
|---|---|---|
| $NH_2$ | $NH_2$ | Na |
| $N(CH_2CH_2OH)_2$ | $NH-CH_3$ | H |
| $NH-CH_3$ | $NH-C_2H_5$ | Na |
| NH-phenyl | $N(CH_3)_2$ | Na |
| $O-CH_3$ | $N(C_2H_5)_2$ | Na |
| O-phenyl | $N(CH_2CH_2OH)_2$ | K |
| $NH_2$ | NH-phenyl | $NH_4$ |
| $NH_2$ | NH-benzyl | H |
| $NH_2$ | NH-CO-phenyl | Na |
| $NH_2$ | $NH-CO-C_4H_9$ | Na |

Compounds having the formula:

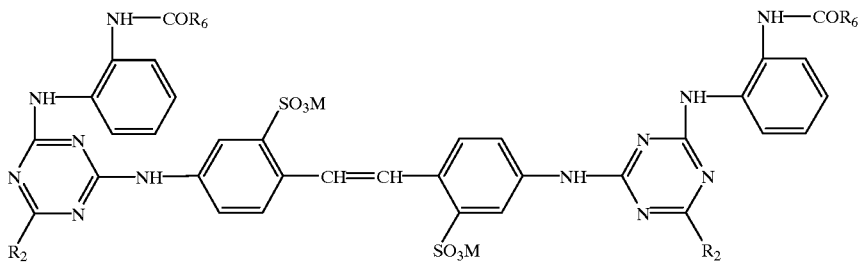

in which the substituents $R_2$, $R_3$ and M are as defined in the following Table:

| $R_2$ | $R_6$ | M |
|---|---|---|
| $NH_2$ | $CH_3$ | H |
| $NH_2$ | $CH_5$ | Na |
| $N(CH_2CH_2OH)_2$ | $CH_2OCH_3$ | H |
| $NH-CH_3$ | $C_2H_5$ | Na |
| NH-phenyl | $CH_3$ | Na |
| $O-CH_3$ | cyclohexyl | Na |
| O-phenyl | $CH_3$ | K |
| $NH_2$ | NH-phenyl | $NH_4$ |
| $NH_2$ | NH-benzyl | H |

EXAMPLE 4

10 g. of cotton fabric swatches are treated in a 200 ml. aqueous solution with either 0 or 0.2% by weight of the test compound (103) (based on the weight of the cotton) and 1 g. of crystalline sodium sulphate, warmed to 20–60° C. over 10 minutes, held at 60° C. for 20 minutes and cooled from 60° C. to 40° C. over 10 minutes. The swatches are then rinsed in cold tap water, dried and ironed.

The whiteness of the treated samples is measured with a DCI/SF 500 spectrophotometer according to the Ganz method. The Ganz method is described in detail in the Ciba-Geigy Review, 1973/1, and also in the article "Whiteness Measurement", ISCC Conference on Fluorescence and the Colorimetry of Fluorescent Materials, Williamsburg, February 1972, published in the Journal of Color and Appearance, 1, No. 5 (1972).

The Sun Protection Factor (SPF) is determined by measurement of the UV light transmitted through the swatch, using a double grating spectrophotometer fitted with an Ulbricht bowl. Calculation of SPF is conducted as described by B. L. Diffey and J. Robson in J. Soc. Cosm. Chem. 40 (1989), pp. 130–131.

The results (an average of 5 measurements at different points on each swatch) are shown in the following Table 1:

TABLE 1

| Example | Test Compound | Ganz Whiteness | SPF |
|---|---|---|---|
| — | none (control) | 65 | 4 |
| 4 | compound (103) | 233 | 31 |

Compared with the control experiment, the SPF value obtained according to the invention is 7–8 times higher and the Ganz Whiteness is also substantially increased.

Similar results are obtained when the compound of formula (103) is replaced by compound (101) or (104).

EXAMPLE 5

A standard (ECE) washing powder is made up from the following components in the indicated proportions (weight %):

8.0% Sodium ($C_{11.5}$)alkylbenzene sulfonate
2.9% Tallow alcohol-tetradecane-ethylene glycol ether (14 mols EO)
3.5% Sodium soap 43.8% Sodium tripolyphosphate
7.5% Sodium silicate
1.9% Magnesium silicate
1.2% Carboxymethyl cellulose
0.2% EDTA
21.2% Sodium sulfate
0 or 0.2% compound (103) and Water to 100%.

A wash liquor is prepared by dissolving 0.8 g. of the above washing powder in 200 mls. of tap water. 10 g. of bleached cotton fabric is added to the bath and washed at 40° C. over 15 minutes and then rinsed, spin-dried and ironed at 160° C. This washing procedure is repeated three and ten times.

After the third and tenth washes, the whiteness of the washed samples is measured with a DCI/SF 500 spectrophotometer according to the Ganz method and the SPF value is determined as described by B. L. Diffey and J. Robson.

The results obtained are set out in the following Table 2:

TABLE 2

| Test | | Ganz Whiteness | | SPF | |
|---|---|---|---|---|---|
| Example | Compound | 3 washes | 10 washes | 3 washes | 10 washes |
| — | none | 61 | 61 | — | 3 |
| 5 | (103) | 197 | 214 | — | 21 |

The results in Table 2 demonstrate that washing with a detergent containing a compound of formula (103) increases the SPF value substantially and improves the Ganz Whiteness (GW) with successive washings.

Similar results are obtained when the compound of formula (103) is replaced by compound (101) or (104).

What is claimed is:

1. A method for increasing the SPF rating of a textile fibre material, comprising treating the textile fibre material with 0.05 to 3.0% by weight, based on the weight of the textile fibre material, of one or more compounds having the formula:

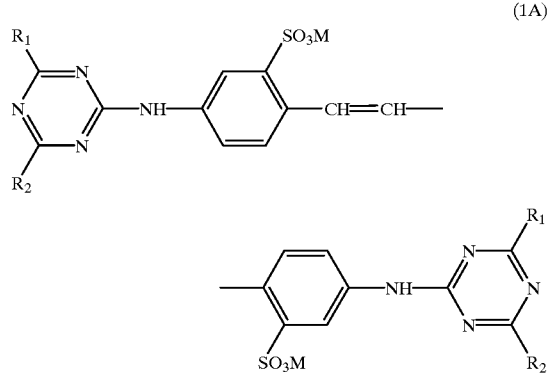

in which M is hydrogen, an alkali metal atom, ammonium or a cation formed from an amine;
$R_1$ is a group having the formula:

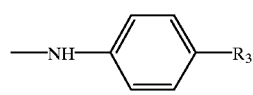

in which $R_3$ is $NR_4R_5$ in which $R_4$ and $R_5$, independently, are hydrogen, $C_1$–$C_4$ alkyl, phenyl or benzyl or NH—CO—$R_6$ in which $R_6$ is $C_1$–$C_4$alkyl, cyclohexyl, phenyl or benzyl;
or the formula:

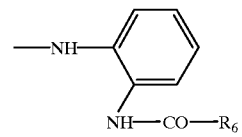

in which $R_6$ has its previous significance; and
$R_2$ is $NH_2$, $N(CH_2CH_2OH)_2$, $N[CH_2CH(OH)CH_3]_2$, NH—$C_1$–$C_4$alkyl, NH-phenyl,

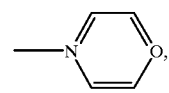

O—$C_1$–$C_4$ alkyl or O-phenyl, provided that the compound of formula (1) in which $R_1$ is

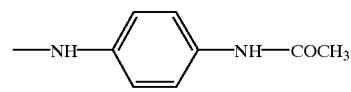

and $R_2$ is

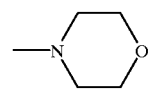

is excluded.

2. A method according to claim 1 in which the textile fibre material is cotton, viscose, flax, rayon, linen, wool, mohair, cashmere, angora and silk, polyester, polyamide or polyacrylonitrile.

3. A method according to claim 2 in which the textile fibre material is cotton, polyamide or wool.

4. A method according to claim 1 in which the textile fibre material has a density of less than 200 g/m² and has not been previously dyed in deep shades.

5. A method according to claim 1 in which the compound of formula (1A) is only sparingly soluble in water and is applied in dispersed form.

6. A method according to claim 1 in which, in addition to the compound of formula (1A), a minor proportion of one or more adjuvants is also be employed.

7. A method according to claim 6 in which the adjuvant is one or more of an emulsifier, perfume, colouring dye, opacifier, further fluorescent whitening agent, bactericide, nonionic surfactant, fabric care ingredient, anti-gelling agent and corrosion inhibitor.

8. A method according to claim 6 in which the amount of each of these adjuvants ranges from 0.01 to 1% by weight on the treated fibre material.

9. A method for increasing the SPF rating of a textile fibre material according to claim 1 comprising washing the textile fibre material with a detergent containing at least one compound of formula (1A), thereby imparting an excellent sun protection factor to the fibre material so washed.

10. A method according to claim 9 comprising washing the textile fibre material at least once with the detergent composition at a temperature ranging from 10 to 100° C.

11. A method according to claim 9 in which the detergent composition used comprises:
   i) 5–90% of an anionic surfactant and/or a nonionic surfactant;
   ii) 5–70% of a builder;
   iii) 0–30% of a peroxide;
   iv) 0–10% of a peroxide activator and/or 0–1% of a bleaching catalyst;
   v) 0.005–2% of at least one compound of formula (1A); and
   vi) 0.005–10% of one or more auxiliaries, each by weight, based on the total weight of the detergent.

12. A method according to claim 1 whereby the tear resistance and/or lightfastness of the treated textile fibre material are also improved.

13. A textile fabric produced from a fibre treated according to a method as claimed in claim 1.

14. An article of clothing produced from a textile fabric according to claim 13.

15. A detergent composition comprising:
   i) 5–90% of an anionic surfactant and/or a nonionic surfactant;
   ii) 5–70% of a builder;
   iii) 0–30% of a peroxide;
   iv) 0–10% of a peroxide activator and/or 0–1% of a bleaching catalyst;
   v) 0.005–2% of at least one compound of formula (1A) as defined in claim 1; and
   vi) 0.005–10% of one or more auxiliaries, each by weight, based on the total weight of the detergent.

16. A detergent composition according to claim 15 comprising:
   i) 5–70% of an anionic surfactant and/or a nonionic surfactant;
   ii) 5–40% of a builder;
   iii) 1–12% of a peroxide;
   iv) 1–6% of a peroxide activator and/or 0.1–3% of a bleaching catalyst;
   v) 0.01–1% of at least one compound of formula (1A); and
   vi) 0.1–5% of of one or more auxiliaries, each by weight, based on the total weight of the detergent.

17. A process for the fluorescent whitening of textile materials or paper comprising contacting the textile materials or paper with at least one compound of formula (1A), as defined in claim 1.

18. A process according to claim 17 in which the textile materials are polyamides, wool or cotton.

19. A method for the protection of human skin comprising covering the skin with an article of clothing according to claim 14.

20. A method according to claim 11 in which the detergent composition used comprises:
   i) 5–70% of an anionic surfactant and/or a nonionic surfactant;
   ii) 5–40% of a builder;
   iii) 1–12% of a peroxide;
   iv) 1–6% of a peroxide activator and/or 0.1–3% of a bleaching catalyst;
   v) 0.01–1% of at least one compound of formula (1A); and
   vi) 0.1–5% of of one or more auxiliaries, each by weight, based on the total weight of the detergent.

21. A method according to claim 11 in which the detergent is formulated as a solid, as an aqueous liquid comprising 5–50% water or as a non-aqueous liquid detergent, containing not more than 5 weight % of water, and based on a suspension of a surface active agent and a builder in a non-ionic surfactant.

22. A method according to claim 11 in which the anionic surfactant component is a sulphate, sulphonate or carboxylate surfactant, or a mixture of these.

23. A method according to claim 11 in which the nonionic surfactant component is a condensate of ethylene oxide with a $C_9$–$C_{15}$ primary alcohol having 3–8 moles of ethylene oxide per mole.

24. A method according to claim 11 in which the builder component is an alkali metal phosphate; a carbonate or bicarbonate; a silicate or disilicate; an aluminosilicate; a polycarboxylate; a polycarboxylic acid; an organic phosphonate; an aminoalkylene poly (alkylene phosphonate); or a mixture of these.

25. A method according to claim 11 in which a peroxide component is present which is any organic or inorganic peroxide compound which bleaches textiles at conventional washing temperatures.

26. A method according to claim 25 in which the peroxide component is a persulphate, perborate or percarbonate.

27. A method according to claim 11 in which the bleaching catalyst is an enzymatic peroxide precursor and/or a metal complex.

28. A method according to claim 11 in which the detergent contains one or more auxiliaries selected from suspending agents; salts for adjusting the pH; foam regulators; salts for adjusting the spray drying and granulating properties; perfumes; antistatic and softening agents; enzymes; photobleaching agents; pigments; and shading agents.

* * * * *